United States Patent
Chapman et al.

(10) Patent No.: US 8,848,871 B2
(45) Date of Patent: Sep. 30, 2014

(54) X-RAY BACKSCATTER IMAGING OF NUCLEAR MATERIALS

(75) Inventors: Jeffrey Allen Chapman, Knoxville, TN (US); John E. Gunning, Oak Ridge, TN (US); Daniel F. Hollenbach, Oak Ridge, TN (US); Larry J. Ott, Knoxville, TN (US); Daniel Shedlock, Knoxville, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 404 days.

(21) Appl. No.: 13/288,168

(22) Filed: Nov. 3, 2011

(65) Prior Publication Data

US 2012/0114102 A1 May 10, 2012

Related U.S. Application Data

(60) Provisional application No. 61/410,117, filed on Nov. 4, 2010.

(51) Int. Cl.
G01N 23/203 (2006.01)

(52) U.S. Cl.
CPC .................................. G01N 23/203 (2013.01)
USPC .................................. 378/87; 378/88; 378/89

(58) Field of Classification Search
CPC .................................................. G01N 23/203
USPC ..................................................... 378/88–90
See application file for complete search history.

(56) References Cited

U.S. PATENT DOCUMENTS

| | | | | |
|---|---|---|---|---|
| 5,181,234 A * | 1/1993 | Smith | | 378/87 |
| 6,094,472 A * | 7/2000 | Smith | | 378/86 |
| 6,151,381 A * | 11/2000 | Grodzins et al. | | 378/90 |
| 6,192,104 B1 * | 2/2001 | Adams et al. | | 378/90 |
| 6,249,567 B1 * | 6/2001 | Rothschild et al. | | 378/88 |
| 6,347,132 B1 * | 2/2002 | Annis | | 378/57 |
| 6,459,764 B1 * | 10/2002 | Chalmers et al. | | 378/88 |
| 6,563,906 B2 * | 5/2003 | Hussein et al. | | 378/89 |
| 6,665,373 B1 * | 12/2003 | Kotowski et al. | | 378/90 |
| 6,754,304 B1 * | 6/2004 | Kumakhov | | 378/45 |
| 6,785,360 B1 * | 8/2004 | Annis | | 378/137 |
| 7,099,434 B2 * | 8/2006 | Adams et al. | | 378/57 |
| 7,110,493 B1 * | 9/2006 | Kotowski et al. | | 378/87 |
| 7,286,638 B2 * | 10/2007 | Ledoux et al. | | 378/57 |
| 7,356,115 B2 * | 4/2008 | Ford et al. | | 378/57 |
| 7,400,701 B1 * | 7/2008 | Cason | | 378/57 |
| 7,551,715 B2 * | 6/2009 | Rothschild et al. | | 378/57 |
| 7,561,666 B2 * | 7/2009 | Annis | | 378/87 |
| 7,796,734 B2 * | 9/2010 | Mastronardi et al. | | 378/90 |
| 7,826,589 B2 * | 11/2010 | Kotowski et al. | | 378/57 |
| 7,924,979 B2 * | 4/2011 | Rothschild | | 378/88 |
| 7,949,097 B2 * | 5/2011 | Bertozzi et al. | | 378/88 |
| 7,957,504 B2 * | 6/2011 | Hill et al. | | 378/45 |
| 8,194,822 B2 * | 6/2012 | Rothschild et al. | | 378/88 |
| 8,325,871 B2 * | 12/2012 | Grodzins et al. | | 376/153 |
| 8,750,454 B2 * | 6/2014 | Gozani et al. | | 378/90 |

* cited by examiner

Primary Examiner — Allen C. Ho

(74) Attorney, Agent, or Firm — Scully, Scott, Murphy & Presser, P.C.

(57) ABSTRACT

The energy of an X-ray beam and critical depth are selected to detect structural discontinuities in a material having an atomic number Z of 57 or greater. The critical depth is selected by adjusting the geometry of a collimator that blocks backscattered radiation so that backscattered X-ray originating from a depth less than the critical depth is not detected. Structures of Lanthanides and Actinides, including nuclear fuel rod materials, can be inspected for structural discontinuities such as gaps, cracks, and chipping employing the backscattered X-ray.

25 Claims, 14 Drawing Sheets

FIG. 1 (Prior Art; Source: Oldenberg)

X-RAY BACKSCATTER IMAGING OF NUCLEAR MATERIALS

CROSS-REFERENCE TO RELATED APPLICATION

The present application claims the benefit of U.S. Provisional Patent Application Publication No. 61/410,117, filed on Nov. 4, 2010, which is herein incorporated by reference in its entirety, including any figures, tables, and drawings.

STATEMENT REGARDING FEDERALLY SPONSORED RESEARCH OR DEVELOPMENT

This disclosure was made with government support under a research project supported by under Contract No. DE-ACO5-000R22725 awarded by the U.S. Department of Energy. The government has certain rights in this disclosure.

FIELD OF THE DISCLOSURE

The present disclosure relates to a method of imaging a nuclear material-including structure employing backscattered X-ray, and a system for implementing the same.

BACKGROUND OF THE DISCLOSURE

When photons impinge on a target, the photons interact with the material of the target in various ways. The mode of interaction between the photons and the material of the target depends on the energy of the photons and the atomic number of the atoms of the material of the object. For example, the graph in FIG. 1 illustrates the dominant photon interaction type as a function of Z and photon energy as originally published in Oldenberg, *Modern Physics For Engineers*, New York, McGraw-Hill (1966).

The angular distribution of Compton scattering shows a clear forward bias (i.e. away from the detector) with increased energy as seen in FIG. 2, which was created using the Wolfram Demonstration Project website (20 Jul. 2010), S. M. Blinder. *Klein-Nishina Formula for Photon-Electron Scattering*. This implies that, despite the increased photon range from higher energy photons and increased probability of Compton scattering in comparison to photoelectric interactions, the net result is that each scattering interaction is less efficient, creating a balance between higher ranger and thus deeper depth penetration but lower efficiency per interaction. The probability is expressed in terms of mass attenuation coefficient ($\mu_t$), with the probability of not interacting and thus not being scattered exponentially decreasing with increased μt and material thickness. Each interaction type has its own μ, such as $\mu_{pe}$ for photoelectric effect and $\mu_{cs}$ for Compton scattering.

Higher energy photons, for the same material, would be more likely to result in scattering events, although each scattering event is less efficient in producing backscatter photons. Similarly, for monoenergetic photons at lower energies, Compton scattering is dominant in low Z materials until it is overtaken by increasing $\mu_{pe}$ relative to $\mu_{cs}$ with increased Z, as seen in FIG. 1. For an ideal single material, $\mu_{cs}$ must be very high in comparison to $\mu_{pe}$ and the actual value for μ must be low enough such that a large proportion of photons do not interact prior to the critical depth. These considerations make it clear that high Z materials are not ideal materials to image using either transmission x-ray imaging or Radiography by Selective Detection (RSD). Low Z materials not only have significantly more Compton scattering at low energies, but a greater proportion of scattering events result in backscatter due to the low energies necessary. For these reasons, imaging of high-Z materials with an X-ray radiation has so far been considered impossible.

SUMMARY OF THE DISCLOSURE

The energy of an X-ray beam and critical depth are selected to detect structural discontinuities in a material having an atomic number Z of 57 or greater. The critical depth is selected by adjusting the geometry of a collimator that blocks backscattered radiation so that backscattered X-ray originating from a depth less than the critical depth is not detected. Structures of Lanthanides and Actinides, including nuclear fuel rod materials, can be inspected for structural discontinuities such as gaps, cracks, and chipping employing the backscattered X-ray.

The x-ray backscatter imaging technique employing the methods of the present disclosure can be employed to examine fuel rods in an economical manner. In this X-ray backscatter imaging method, the detectors are on the same side of what is being imaged as the x-ray source. The X-ray source and detectors can be positionally fixed relative to each other.

Since the X-ray does not need to travel through the entire thickness of material, the upper section of objects that cannot be imaged using transmission imaging can be imaged using backscatter imaging. Thus, the cladding, gap and outer edge of the fuel pellets can be imaged employing the methods of the present disclosure.

According to an aspect of the present disclosure, a method is provided to image a high-Z material-including structure by X-ray backscatter imaging. The method includes: irradiating a target including a high-Z material-including structure with an incident X-ray radiation from an X-ray source, the high-Z material-including structure including at least one element having an atomic number of at least 57; detecting a backscattered X-ray radiation from the target with at least one detector-collimator assembly positioned to block a fraction of the backscattered X-ray radiation originating at depths less than a critical depth from a top surface of the target; and constructing an image of the target employing at least data collected at the at least one detector-collimator assembly, the image including information on structural discontinuity of the high-Z material-including structure.

According to another aspect of the present disclosure, a system including an apparatus for generating an X-ray backscatter image and a target is provided. The target includes a high-Z material-including structure, which includes at least one element having an atomic number of at least 57. The apparatus includes: an X-ray source configured to emit an X-ray radiation; a target holder that holds the target; at least one detector-collimator assembly configured to detect a backscattered X-ray radiation from the target and is positioned so as to block a fraction of the backscattered X-ray radiation originating at depths less than a critical depth from a top surface of the target; and a computing device configured to receive data collected at the at least one detector-collimator assembly, and configured to construct an image of the target employing the data, the image including information on structural discontinuity of the high-Z material-including structure.

DETAILED DESCRIPTION OF THE DISCLOSURE

Figure 1:
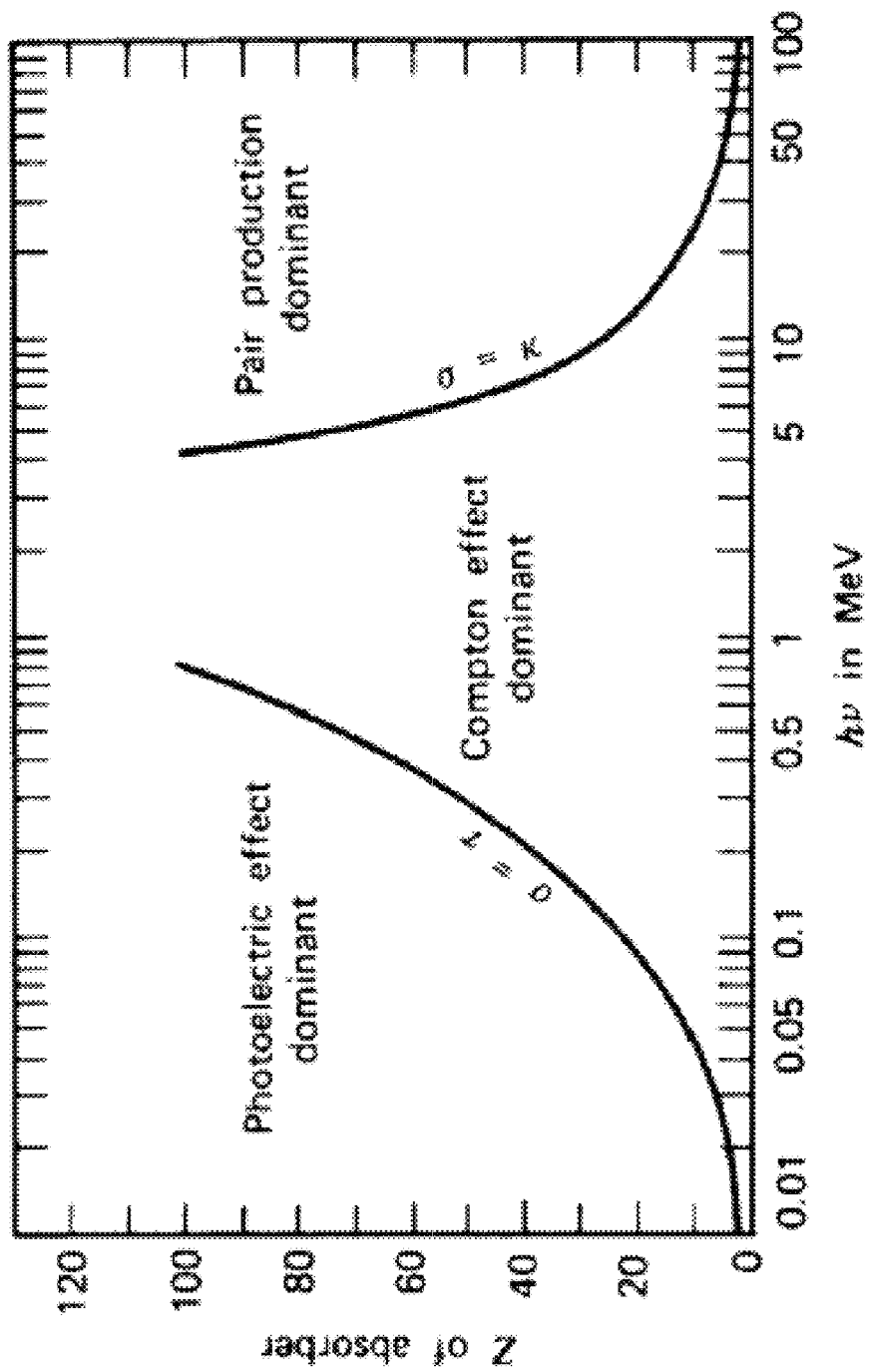
FIG. 1 is a graph illustrating the predominant mode of interaction between light and matter as a function of the photon energy and the atomic number of a target material.
Figure 2:
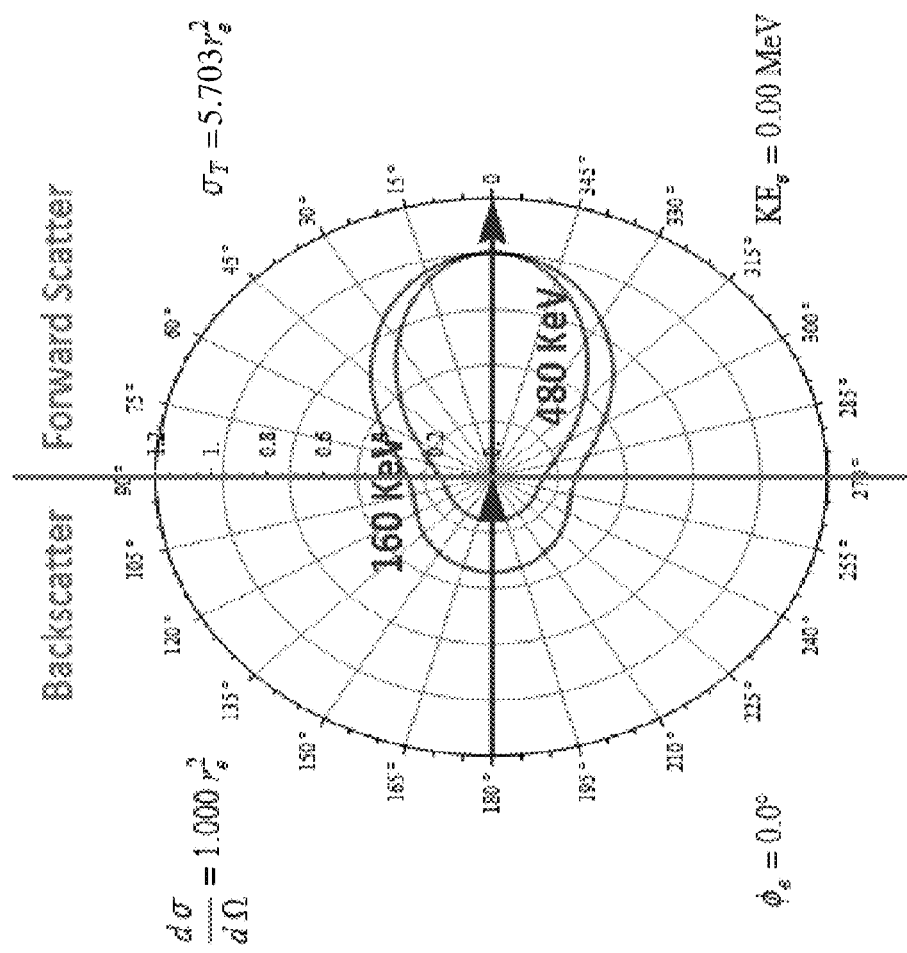
FIG. 2 is the Klein-Nishina cross-section distribution for 480 kVp and 160 kVp photons. Plot generated using Wolfram Mathematica

As stated above, the present disclosure relates to a method of imaging a nuclear material-including structure employing backscattered X-ray, and a system for implementing the same, which are now described in detail with accompanying figures. It is noted that like and corresponding elements mentioned herein and illustrated in the drawings are referred to by like reference numerals. It is also noted that proportions of various elements in the accompanying figures are not drawn to scale to enable clear illustration of elements having smaller dimensions relative to other elements having larger dimensions.

Nuclear power has provided safe, sustainable, carbon-free, large-scale electricity generation for almost half a century. Fuel rod integrity has increase significantly and has reached a level such that a burnup approaching 50 GWd/MTU can be achieved with only about 0.001% of the fuel rods developing leaks. Efforts are underway to develop advanced nuclear fuels for both existing and next generation reactors that can achieve higher power densities and burnups without developing leaks in the fuel rods. However, fuel and cladding stability issues currently limit the fuel power density and burnup. A better understanding of these issues and associated limitations on fuel performance are needed to improve the performance of the fuel and enable nuclear reactors to produce more energy at higher power levels for the same amount of fuel.

Although only a small percentage of fuel rods develop leaks, leaks have a significant effect on the overall cost of reactor operations. When any fuel rod leaks, fission gases escape contaminating the reactor coolant and system, and if sufficiently severe requiring derating of assemblies (operating at lower power) and/or reactor shutdown and removal of the leaking assemblies (thus additional lost generating capacity). A better understanding of the mechanisms that cause the fuel cladding to fail and a method for detecting potential internal flaws would produce a significant overall cost savings and help accomplish the stated industry objective of zero leakers.

An embodiment of the present disclosure enables characterizing both a complete fuel rod and individual fuel pellets to a resolution of less than one millimeter. A highly focused high-energy scanning X-ray beam and a suitable arrangement of detectors is used to create 3-dimensional images with sufficient resolution to examine fuel rods for manufacturing defects, thus eliminating potentially leaking fuel rods.

Most fuel rod leaks are caused by fretting, which is the rubbing of the cladding against the rod supports, or by stress corrosion cracking. However, the root cause of a significant fraction of the leakers is unknown but is hypothesized to be caused by $UO_2$ chips breaking off from the edges of the fuel pellets and getting caught between the pellet and cladding.

There is no current method for checking the integrity of the fuel rods once the end caps are welded in place. Several methods have been investigated to image the fuel pellets in the rods. Standard transmission λ-ray imaging does not work because the X-ray energy needs to be in the range of 1 MeV to penetrate the $UO_2$. The density of the fuel is likely to mask small cracks in the fuel. Also, since this is beyond the range of current X-ray tubes a linear accelerator would be required to reach these energies. Use of a linear accelerator to generate X-ray at an energy greater than 1 MeV is a cost prohibitive method, and requires significantly more complex manipulation for image generation than X-ray methods. Backscatter imaging using neutrons has also been tried with no success, as has thermal imaging of the fuel rods.

There are six general categories of problems that cause fuel rod failures: Grid-to-Rod fretting, crud/corrosion, pellet clad interaction-stress corrosion cracking (PCI-SCC), debris, fabrication, and unknown. The categories of problems that are detectable by the methods of the present disclosure include, but are not limited to, fabrication, PCI-SCC, and unknown. It is noted that the fabrication category make up 2-8% of the failures, the PCI-SCC category make up about 10% of the failures, and unknown make up about 25% of the failures. Being able to identify and exclude from the fuel bundle fuel rods that have characteristics consistent with potential leakers would reduce, and eventually eliminate, the resultant reactor power degradations or shutdowns from rods damaged during manufacturing, and help identify unknown failure mechanisms.

There are two significant issues that need to be addressed concerning existing nuclear fuel: actual $UO_2$ fuel pellets and the cladding. The methods of embodiments of the present disclosure enable a study of the significance of the anomalies to fuel integrity, and allow redesign of nuclear fuel rods and/or modification of manufacturing processes to prevent the occurrence of the problems. The methods of the present disclosure can also serve as part of the fuel qualification process at the fuel fabrication facility to ensure manufactured fuel rods are free of defects that could result in rod failures.

By enabling the imaging fuel pellets and rods, embodiments of the present disclosure can facilitate the development of more reliable and efficient fuel (and fuel rods) for current and advanced reactor systems.

In one embodiment, nuclear fuel rods can be inspected for defects employing x-ray backscattering radiography. Standard nuclear fuel rods include $UO_2$ pellets having a diameter from about 0.7 cm to about 2.5 cm, and are encased in a zirconium alloy cladding. A small but significant number of these rods develop leaks while in the reactor, which release radioactive fission products into the coolant, and cause the power reactor to down rate (decrease power) or possibly shut down. Reducing or eliminating leaking fuel rods would enhance nuclear safety and reduce energy costs.

In the course of research leading to the present disclosure, capabilities of X-ray backscatter imaging methods to examine high Z materials, such as $UO_2$, have been demonstrated. In X-ray backscatter imaging, the detectors are on the same side of what is being imaged as the X-ray source. The detectors see only those X-ray photons that rebound from the material at close to 180 degrees. The X-ray source and detectors are fixed relative to each other. The assembly (including of the source and detectors) is rotated around the fuel rod, and is translated along its entire length. The strength of the returned signal is an indication of the type of material at that location in the fuel rod. The diameter of the X-ray beam, distance between intervals at which measurements are recorded, and length of time for each interval can be varied to produce as detailed an image as needed. Additionally, at each interval multiple measurements can be made varying the length of an aperture that shields the detector from returning X-rays above a selected level to produce depth information.

According to an embodiment of the present disclosure, subsurface characteristics can be imaged in geometries where only the front surface is readily reachable. Backscatter imaging uses only the photons that scatter about 180 degrees back off material due to Compton scattering. Computer Tomography (CT) and backscatter techniques can be combined to optimize image quality, and to minimize irradiation time and dose, producing detailed 3-dimensional images of structures.

Figure 3:
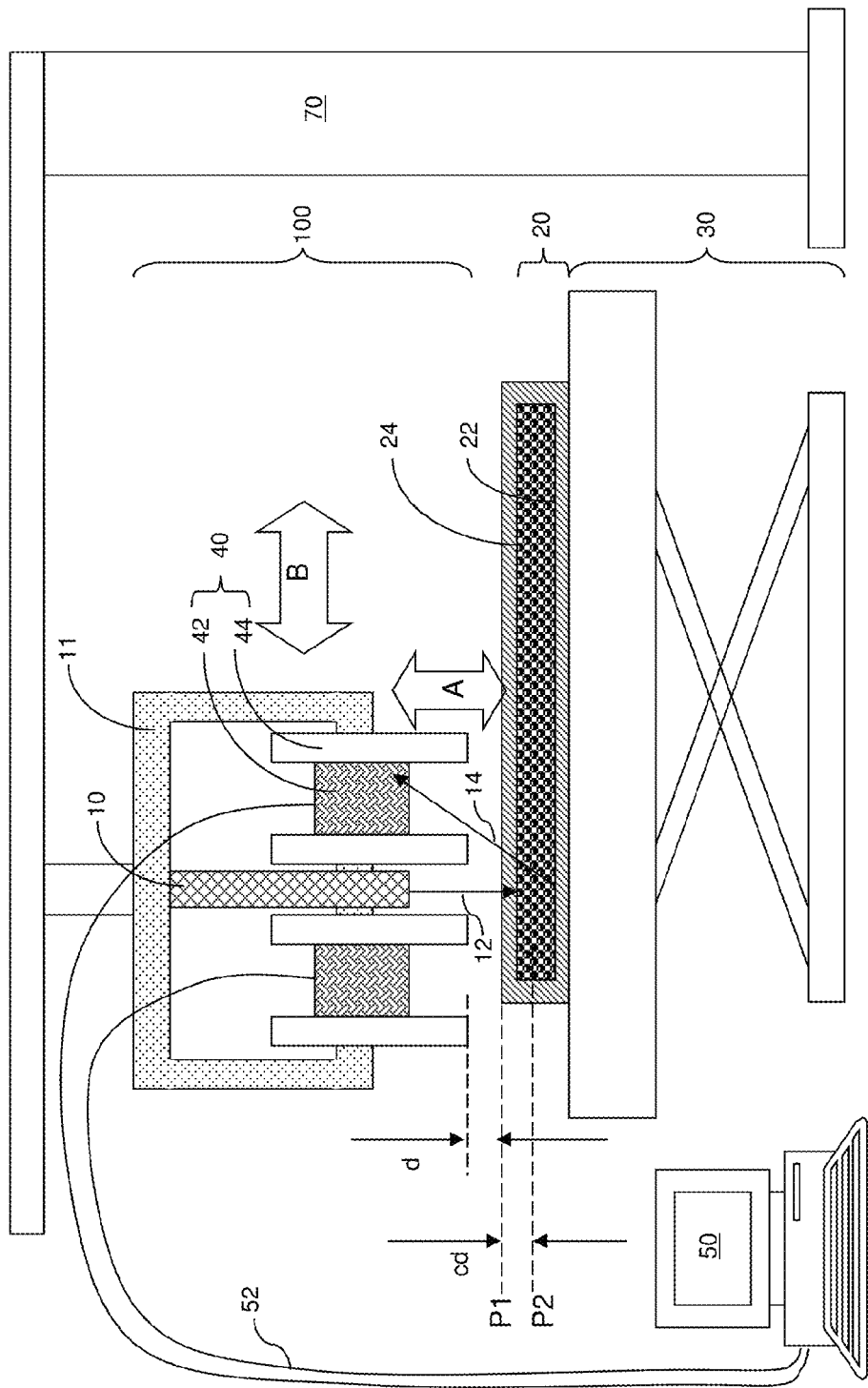
FIG. 3 is a vertical cross-sectional view of an exemplary system for imaging a high-Z material-including structure with backscatter X-ray imaging according to an embodiment of the present disclosure.

Referring to FIG. 3, an exemplary system for generating an X-ray backscatter image of a high-Z material-including structure 22 is illustrated according to an embodiment of the present disclosure. The exemplary system includes an apparatus for X-ray backscatter imaging of a target 20.

The target 20 includes a high-Z material-including structure 22, which includes a high-Z material. As used herein, a "high-Z material" refers to a material having an atomic number Z of Lanthanum or greater, i.e., having an atomic number of 57 or greater.

The target 20 includes at least one element that is a high-Z material. In one embodiment, the atomic concentration of at least one high-Z material in the high-Z material-including structure 22 can be from 0.01% to 100%. In one embodiment, the atomic concentration of at least one high-Z material in the high-Z material-including structure 22 can be from 0.1% to 50%. In one embodiment, the atomic concentration of at least one high-Z material in the high-Z material-including structure 22 can be from 1% to 50%. In one embodiment, the atomic concentration of at least one high-Z material in the high-Z material-including structure 22 can be from 10% to 50%.

In one embodiment, at least one element is selected from Lanthanides and Actinides. In one embodiment, the at least one element is a fissile material such as uranium, thorium, and plutonium.

In one embodiment, the high-Z material including structure 22 includes an oxide, a nitride, a carbide, a fluoride, or a boride of the at least one element.

In one embodiment, the high-Z material-including structure 22 includes a nuclear fuel material that is encased in a cladding 24. In one embodiment, the high-Z material can include $UO_2$.

In one embodiment, the high-Z material-including structure 22 can include a manufactured nuclear fuel rod in which atomic ratio of fissile atoms to fission products is greater than 5:1. In another embodiment, the high-Z material-including structure 22 can include a spent nuclear fuel rod that has been removed from a nuclear reactor.

The apparatus includes a source-detector assembly 100, a target holder 30, a source-detector assembly mounting structure 70, a computing device 50, and other optional peripheral components. The source-detector assembly 100 includes an X-ray source 10, at least one detector-collimator assembly 40, and a source-detector frame 11.

The X-ray source 10 is configured to emit X-ray radiation, which is directed to the target 20 as a collimated beam. The X-ray radiation directed to the target is herein referred to as incident X-ray radiation 12. As used herein, X-ray radiation is electromagnetic radiation having a wavelength in the range of 0.01 nm to 10 nm in free space. The X-ray source 10 can includes an aperture plate including a material that absorbs X-ray.

Figure 5:
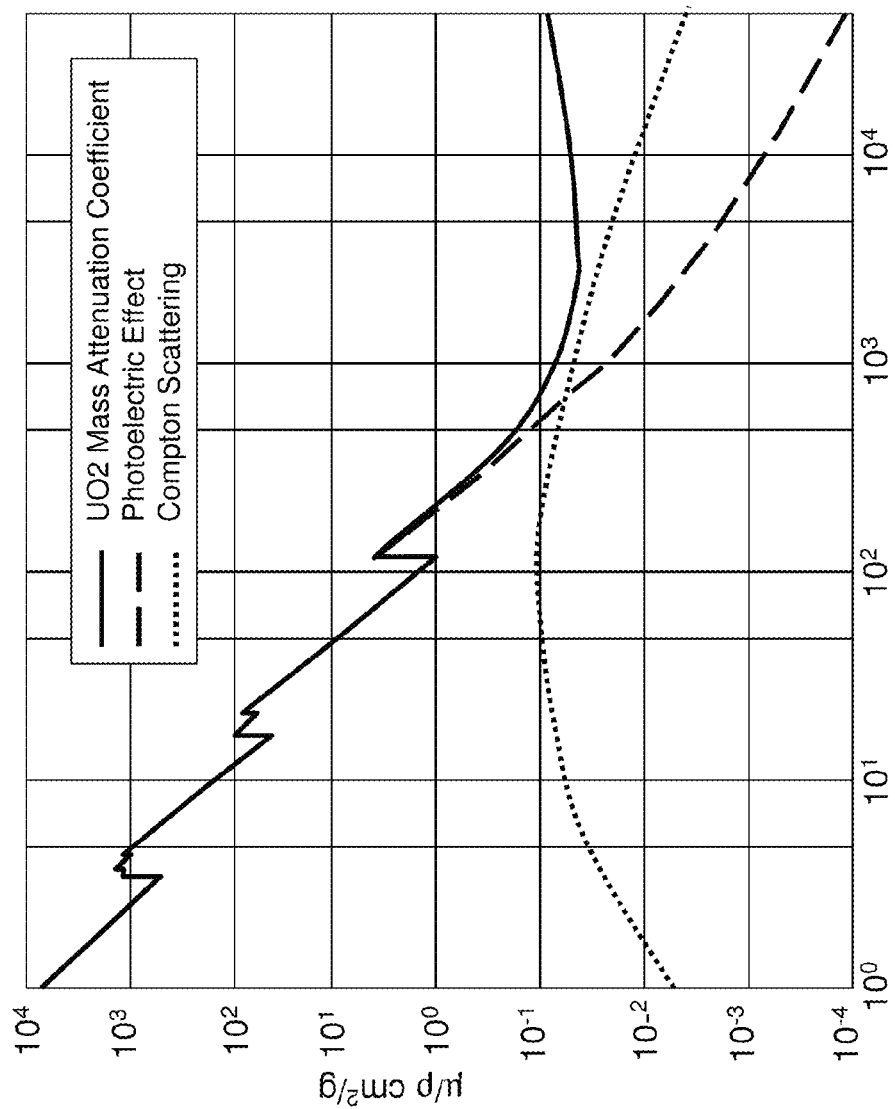
FIG. 5 is the Mass attenuation coefficients plot for $UO_2$ created in XMUDAT.

The energy of the photons in the incident X-ray radiation is selected to compromise two important parameters to be considered. The first parameter is the numerical value for a total mass attenuation coefficient $\mu$ of the high-Z material in the target 20. The second parameter is the relative values of the individual photoelectric (absorption) and Compton scatter (scattering) attenuation coefficients within the total mass attenuation coefficient $\mu$ of the high-Z material in the target 20. Numerically, $\mu$ tends to decrease with increased photon energy, with the exception of large positive vertical shifts at specific energies as shown in FIG. 5, which depend on the material due to the discrete binding energy for each electron shell.

In one embodiment, the energy of the photons generated by the X-ray source 10 can be selected to be in a range from 150 keV to 800 keV.

In one embodiment, at least one element having an atomic number of at least 57 within the high-Z material-including structure 22 is an Actinide, and the X-ray radiation 12 emitted from the X-ray source 10 includes photons having energy in a range from 500 keV to 700 keV. In one embodiment, the Actinide can be uranium, and the high-Z material-including structure 22 can include $UO_2$.

The detector-collimator assembly 40 can be a single detector-collimator assembly 40 or a plurality of detector-collimator assemblies 40. Each of at least one detector-collimator assembly 40 includes a detector 42 and a collimator 44. The detector 42 is recessed relative to an opening in the collimator 44 that face the target 20. Each detector-collimator assembly 40 is configured to detect backscattered X-ray radiation 14 from target 20. Further, each detector-collimator assembly 40 is positioned so as to block a fraction of the backscattered X-ray radiation 14 originating at depths less than a critical depth "cd" from a top surface of the target 20.

During operation of the exemplary apparatus, a fraction of the incident X-ray radiation 12 is backscattered from the target 20 as the backscattered X-ray radiation 14. If the backscattered X-ray radiation 14 reaches any of the at least one detector 42, that detector 42 detects the photon of the backscattered X-ray radiation 14. The detection of the photon by a detector 42 is registered as a detection event at that detector 42, which constitutes a data. Each detector 42 can be a device for detecting x-ray radiation as known in the art such as a scintillation detector.

The critical depth "cd" of each detector-collimator assembly 40 is defined as the minimum depth at which a photon whose direction of movement can undergo a single scattering reaction, scatter into the detector's active volume without passing through the collimator surrounding the detector's active volume. The critical depth "cd" is given by trigonometric considerations involving collimator length, detector size, and detector position parameters.

Figure 4:
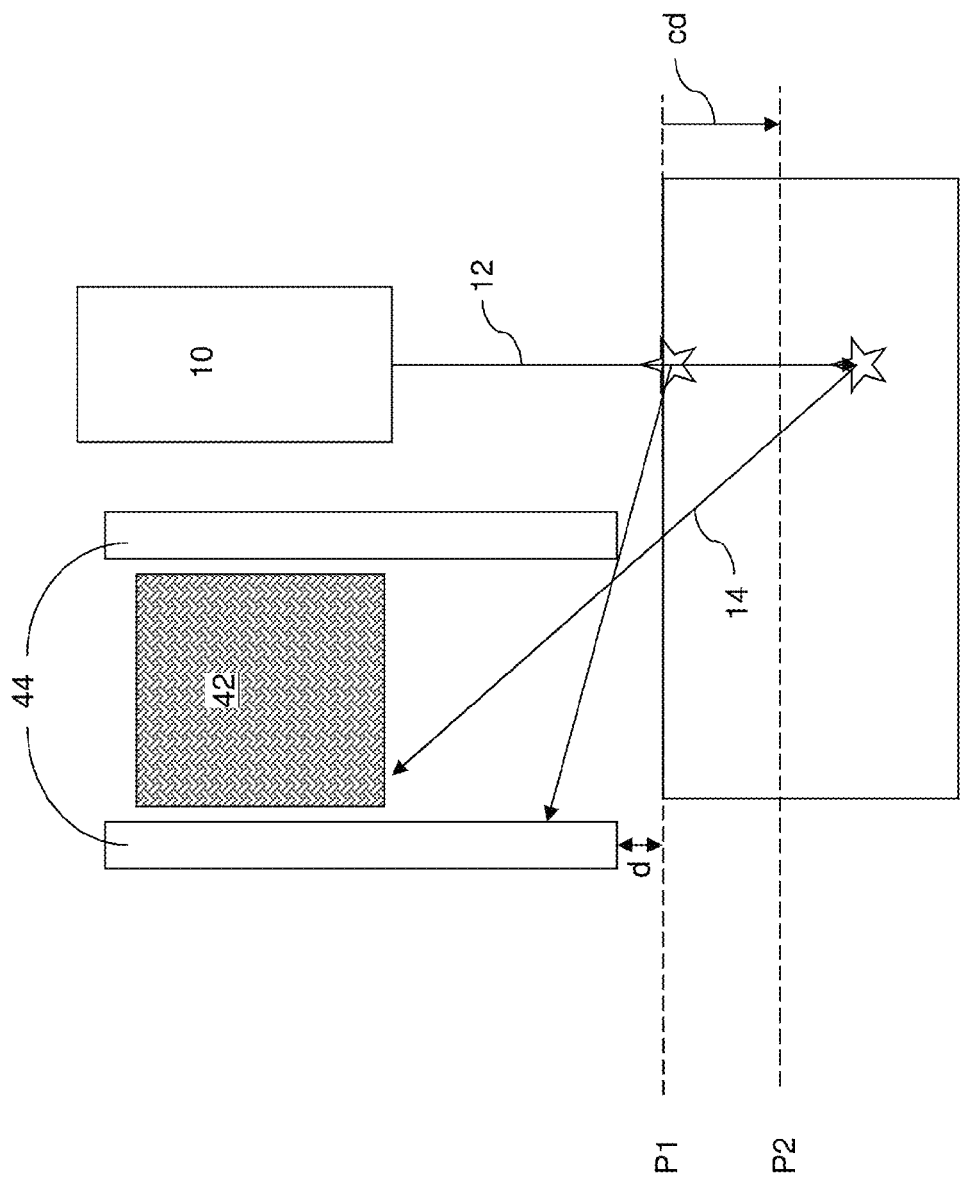
FIG. 4 is a magnified view of a portion of the target, the X-ray source, and a detector-collimator assembly of FIG. 3.

The concept of critical depth for a collimated system is shown in FIG. 4. FIG. 4 demonstrates that photons which scatter above a critical depth "cd" are not detected by the detector 42, while photons which scatter below the critical depth cd are capable of being detected. The detector position parameters include a lateral offset of each detector 42 relative to the point of incidence of the incident X-ray radiation 12 at the top surface of the target 20. The plane including the top surface of the target 20 is represented by a first plane P1. Further, the detector position parameters include at least one distance "d", each of which is a vertical separation distance between each collimator 44 and the first plane P1. As a result of creating the critical depth "cd", single interaction photons can only be detected if they do not interact prior to reaching the critical depth "cd", undergo a collision below the critical depth cd in the direction of the detector 42, and do not interact until reaching the detector active area. The plane that is parallel to the first plane P1 and is located at the critical depth cd is herein represented as a second plane P2.

In one embodiment, the target 20 can include a stack of the high-Z material-including structure 22 and the cladding 24 that encloses the high-Z material-including structure 22. The critical depth "cd" can be within the high-Z material-including structure 22 during the irradiation of the target 20 with the incident X-ray radiation 12 and concurrent detection of the backscattered X-ray radiation 14 with the at least one detector-collimator assembly 40.

The source-detector frame 11 is a mechanical structure configured to mechanically support the X-ray source 10 and the at least one detector-collimator assembly 40, and to maintain the relative positions of the X-ray source 10 and the at least one detector-collimator assembly 40 during at least one scan of the target 20 with incident X-ray radiation 12. As discussed below, the relative positions of the X-ray source 10 and the at least one detector-collimator assembly 40 remain stationary during each of the at least one scan of the target 20.

The target holder 30 is a mechanical structure configured to hold the target 20 during the at least one scanning of the target 20. The target holder 30 can be configured to be stationary, to move in a linear movement along a direction, or to cause movement of the target 20 relative to the center of mass of the target holder 30.

The source-detector assembly mounting structure 70 is a mechanical structure configured to hold the source-detector assembly 100. The source-detector assembly mounting structure 70 can be configured to hold the source-detector assembly 100 stationary, to move the source-detector assembly 100 in a linear movement along a direction. The source-detector assembly mounting structure 70 can be configured to be affixed to a permanent mounting structure such as a floor of a building or ground, or can be temporarily affixed to a floor of a building or ground employing methods known in the art.

The computing device 50 is configured to receive data collected at the at least one detector-collimator assembly 40, and is configured to construct an image of the target 20 employing the data. The data can be transmitted from each of the at least one detector 42 to the computing device 50 via a signal transmission cable 52, which is a peripheral component. Additional peripheral components can be provided to facilitate the interface between humans and the computing device 50 and/or to facilitate additional signal transmission or image processing.

The computing device 50 can be, for example, a computer as known in the art, or other mobile or immobile devices configured to analyze data from the at least one detector 42. The data collected by the computing device 50 represents magnitude and/or spatial distribution of the backscattered X-ray radiation 14 at any given setting of a combination of a scanned area and the critical depth cd.

The image constructed by the computing device 50 includes at least information on structural discontinuity of the high-Z material-including structure 22. Information on structural discontinuity herein refers to any type of discontinuity in a physical structure, and includes, but is not limited to, cracks, chipping, gaps, and any other type of cavity or foreign material in a material matrix.

The exemplary system of FIG. 3 can be employed to image a material by X-ray backscatter imaging. Specifically, the target 20, which includes the high-Z material-including structure 22, is irradiated with the incident X-ray radiation 12 from the X-ray source 10. As discussed above, the high-Z material-including structure 22 includes at least one element having an atomic number of at least 57.

The backscattered X-ray radiation 14 from the target 20 is detected with the at least one detector-collimator assembly 40, which is positioned to block a fraction of the backscattered X-ray radiation 14 originating at depths less than the critical depth "cd" from the top surface of the target 20.

In one embodiment, different areas of the target 20 are scanned at least once with the incident X-ray radiation 12 by providing a relative movement between the target 20 and the X-ray source 10. During each scanning, the distance d between the target 20 and each of the at least one detector-collimator assembly 40 can be maintained at a constant value.

In one embodiment, the relative movement between the target 20 and the X-ray source 10 can be tailored to enable scanning of the entire area of the target 20. In one embodiment, the target 20 can be a nuclear fuel rod, plate, or other geometry containing nuclear fuel, and the direction of the relative movement between the target 20 and the X-ray source 10 can be along the lengthwise direction of the nuclear fuel rod, plate or other geometry.

In one embodiment, the relative movement between the target 20 and the X-ray source 10 is provided continuously while the target 20 is continuously irradiated with the incident X-ray radiation 12.

In another embodiment, the relative movement between the target 20 and the X-ray source 10 is provided between each sequential irradiation of different areas of the target 20 with the incident X-ray radiation 12.

In one embodiment, the target 20 and the X-ray source 10 can be configured to move relative to each other while the relative position between the X-ray source 10 and each of the at least one detector-collimator assembly 40 remains stationary.

In one embodiment, the relative movement between the target 20 and the X-ray source 10 can be provided by maintaining the target 20 stationary and moving the X-ray source 10 and the at least one detector-collimator assembly 40. The X-ray source 10 and the at least one detector-collimator assembly 40 can move at the same rate of movement in a same direction throughout the relative movement, i.e., can be stationary relative to each other during this relative movement between the target 20 and the X-ray source 10.

In one embodiment, the target 20 can be a nuclear fuel rod, and the relative movement is provided by moving the X-ray source 10 and the at least one detector-collimator 40 along the lengthwise direction of the nuclear fuel rod.

In one embodiment, the relative movement between the target 20 and the X-ray source 10 can be provided by maintaining the X-ray source 10 and the at least one detector-collimator assembly 40 stationary while moving the target 20.

In one embodiment, the source-detector assembly 100 can be rotated around the target 20, and can be translated along the entire length of the target 20.

During the scanning, the strength of the returned signal is an indication of the type of material at that location in the target 20. The diameter of the X-ray beam, distance between intervals at which measurements are recorded, and length of time for each interval can be varied to produce as detailed an image as needed. Additionally, at each interval multiple measurements can be made varying the length of an aperture that shields the detector 42 from returning X-rays above a selected level to produce depth information.

In one embodiment, multiple scans can be performed at different settings for the critical depth "cd". In order to change the critical depth "cd", for example, to a second critical depth that is different from the critical depth "cd", the distance "d" between the at least one detector-collimator assembly 40 and the target 20 can be changed. The at least one detector-collimator assembly 40 becomes positioned to block a fraction of the backscattered X-ray radiation 14 originating at depths less than the second critical depth from the top surface of the target 20.

The target 20 can be irradiated with the incident X-ray radiation 12 from the X-ray source 10 while the changed distance is maintained, i.e., while at least one detector-collimator assembly 40 becomes positioned to block a fraction of the backscattered X-ray radiation 14 originating at depths less than the second critical depth from the top surface of the target 20. A relative movement between the target 20 and the X-ray source 10 can be provided to scan the target 20 while the setting for the critical depth "cd" is set at the second critical depth.

The change of the critical depth and a subsequent scanning can be repeated multiple times to provide data on the structural discontinuity of the high-Z material-including structure 22 at different depths from the surface.

Further, the target 20 can be rolled over and scanned again with at least one setting for the critical depth "cd" so that different sides of the target 20 can be imaged in successive scans.

The image of the target 20 is constructed by processing the data collected at the at least one detector-collimator assembly 40 with the computing device 50. The computing device 50 constructs the image of the target 20 employing a combination of a pre-loaded imaging software and the data collected at the at least one detector-collimator assembly 40. The pre-loaded imaging software converts digital signals from the at least one detector-collimator assembly 40 into at least one image. The imaging software can include algorithms such as contrast limited adaptive histogram equalization (CLAHE), a combination of adaptive equalization and application of Wiener filter, a combination of adaptive equalization and application of a median filter, fast Fourier transformation, or any other image processing algorithms for generating an image from a set of discrete data points as known in the art. As discussed above, the image includes information on structural discontinuity of the high-Z material-including structure 22.

The image of the target 20 can be generated based on data collected at the at least one detector-collimator assembly 40 during a single scan during which the critical depth "cd" remains constant, or can be generated based on data collected at the at least one detector-collimator assembly 40 during multiple scans with different settings for the critical depth cd.

In one embodiment, multiple images of the target 20 can be generated based on data collected at the at least one detector-collimator assembly 40 during multiple scans with different settings for the critical depth "cd". In one embodiment, an image of the target 20 can be generated for each setting for the critical depth "cd" from the data collected at the at least one detector-collimator assembly 40 while that setting for the critical depth "cd" is maintained. Each image of the target 20 can include information on structural discontinuity of the high-Z material-including structure 22.

In one embodiment, each of the multiple images of the target 20 at different settings for the critical depth "cd" can be a 2-dimensional image. In one embodiment, a 3-dimensional image of the target 20 can be constructed from a set of images including the multiple images.

In one embodiment, a 3-dimensional image of the target 20 can be constructed, without constructing 2-dimensional images, from the various data sets that are collected at the at least one detector-collimator assembly 40 at different settings for the critical depth "cd".

Standard CT imaging techniques do not work well for high-Z materials due to the inability of lower energy X-rays to sufficiently penetrate these materials. However, computer simulations performed in the course of the research leading to the present disclosure show that X-ray photons having energy in the range of 600 keV or greater is able to image structures up to 1 cm deep inside $UO_2$, and significantly deeper in lower Z material. In one embodiment of the present disclosure, X-ray photons having energy in the range of 600 keV or greater are able to image both fuel pellets and fuel rods.

As discussed above, the high-Z material-including structure 22 can include a nuclear fuel material that is encased in a cladding 24. The target 20 can thus include a stack of the high-Z material-including structure 22 and the cladding 24 that encloses the high-Z material-including structure 22. By setting the critical depth "cd" at a value that places the second plane P2 within the high-Z material-including structure 22, the nuclear fuel material can be imaged employing the exemplary apparatus of the present disclosure.

In one embodiment of the present disclosure, significantly lower X-ray energies can be used to image only the fuel rod cladding and $UO_2$ outer layer, looking for defects.

In one embodiment, use of X-ray backscattering to image pellets and/or cladding in fuel rods makes it possible to produce 3-dimensional images of high-Z materials such as $UO_2$ and zirconium found in fuel pellets and assembled fuel.

One of the primary mechanisms that cause fuel rods to leak are small chips from the edge of fuel pellets that break off and get caught between the pellet outer surface and the cladding inner wall. These chips result in hot spots and stress risers in the rod cladding. The resultant interaction between the $UO_2$ and cladding causes a weakening of the cladding wall that eventually fails. In one embodiment of the present disclosure, fuel rods can be imaged after manufacturing as a final quality assurance check. This application has the potential to detect this type of defect prior to using the rod in a fuel rod assembly, and thus eliminate the potential for leaking fuel rods from this type of event.

Current practical burnup limits are primarily set to minimize leaking fuel rods. If the rods that begin to leak at or below a specified burnup can be eliminated, fuel could be burned to higher levels allowing more of the uranium in existing fuel rods to be utilized. In one embodiment of the present disclosure, spent fuel rods that have been identified as leakers can be imaged.

In another embodiment of the present disclosure, imaging of fuel rods can be employed in the non-destructive examination phase of post-irradiation examination (PIE) of irradiated fuel rods. This application allows a detailed image to be generated prior to cutting open the rod (destructive PIE), and thus potentially destroying valuable evidence of failure modes. Thus, imaging leaking spent fuel rods can aid in understanding the causes of the cladding damage that results in leaking fuel.

In one embodiment of the present disclosure, a 3-dimensional imaging system for analyzing a fuel rod/pellet. This 3-dimensional imaging system can be employed for nuclear fuels research and/or as part of a fuel rod quality verification system in manufacturing fuel bundles. The 3-dimensional imaging system includes an X-ray source, photosensitive detectors, and a computing device embodying a mathematical model-based program employed to deconvolve signals detected at the photosensitive detectors into 3-dimensional images. Several detectors are positioned around the object being imaged, which can be a nuclear fuel. The photosensitive detectors can be collimated, shielded, and positioned in various configurations in order to optimize the signal return, and to minimize background noise.

In one embodiment, the 3-dimensional imaging system can be employed to detect anomalies in completed unirradiated fuel rods (including welds), on the order or 0.1 mm to 1.0 mm, by scanning the entire fuel rod in about 1 minute.

By analyzing the results from several detectors positioned around the object under examination, a detailed 3-dimensional image can be generated more rapidly than using CT or backscatter imaging alone.

The computing device of the 3-dimensional imaging system can include electronics, controllers, and software that are employed to operate the 3-dimensional imaging system. The software controls the overall operation of the 3-dimensional imaging system, signal acquisition, signal processing (image reconstruction), and image display. Operation of the X-ray source can be supported by an X-ray controller, chillers, high voltage equipment, and photosensitive detectors and related peripheral components. In addition, a target support structure configured to hold, move, and rotate the target under examination is provided. The target support structure can be configured to hold nuclear fuel rods as known in the art.

Non-irradiated and irradiated fuel rods and pellets can be imaged using the 3-dimensional imaging system.

The 3-dimensional imaging system of the present disclosure can also be employed to image the contents of sealed packages such as drums, crates, or shipping containers without opening them. For example, the 3-dimensional imaging system of the present disclosure can be employed at ports of entry or any border crossing were large numbers of closed containers need to be rapidly checked. The 3-dimensional imaging system of the present disclosure can also be used to scan for contraband hidden internally at border crossings and checkpoints.

In addition, the 3-dimensional imaging system of the present disclosure can be employed to image suspect nuclear and non-nuclear materials/containers, and to support nuclear nonproliferation and safeguards activities.

Further, the 3-dimensional imaging system of the present disclosure can be employed to perform a rapid, 3-dimensional, whole body scan. This type of scan would be useful for medical diagnostics of cancer as well as major trauma to the body.

EXAMPLE

The backscatter x-ray imaging technique of Radiography by Selective Detection (RSD) was investigated for its ability to determine defect presence and type in a $UO_2$ fuel rod surrounded by Zirconium cladding. A fuel rod was simulated by a rectangular parallelepiped with Zirconium cladding, and pencil beam x-ray sources of 160 kV (79 KeV avg) and 480 kV (218 KeV avg) were generated using Monte Carlo N-Particle transport code (MCNP) to attempt to image void and Pd defects in the interior of the fuel pellet and on the surface of the pellet. It was found that the 160 kV spectrum was unable to detect the presence of interior defects, while the 480 kV spectrum was able to with both the backscatter and RSD methods, though was very inefficient with the RSD method. It was also found that both energy spectrums were able to detect both defects in the surface defect case using both imaging methods. Additionally, two simulation fuel rods were imaged using a backscatter x-ray imaging system. It was found that the system used was capable of detecting individual Hf pellets in a Zircaloy-4 cladding, and may be capable of detecting individual steel pellets in a steel cladding. It is expected that the system used would also be capable of detecting individual $UO_2$ pellets in a Zircaloy-4 cladding, though no $UO_2$ fuel rod was available for imaging.

Methods and Materials—Monte Carlo N-Particle Transport Code (MCNP) and Geometry

Figure 6:
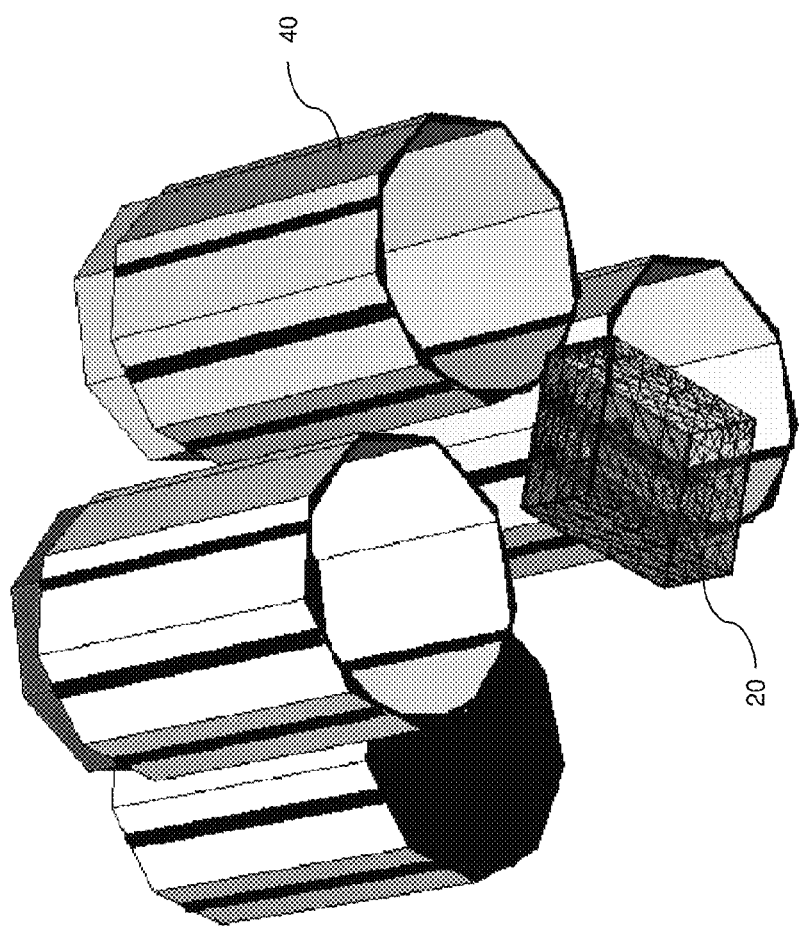
FIG. 6 illustrates a fully collimated test case for a backscatter system. This image was made in the MCNP Visual Editor.

The Monte Carlo N-Particle Transport Code (MCNP) is a general-purpose radiation transport code that was used to simulate a four-detector RSD system performing a raster scan of a fuel rod model. The RSD system was designed to represent an RSD system created and used at The University of Florida consisting of four collimated, cylindrical NaI detectors (5.08 cm diameter) centered around a pencil beam photon source of a continuous-energy X-ray spectrum. The lower surface of each detector was 5 cm above the top surface of the fuel rod representation, with collimation in test cases reaching critical depths of 0, 0.15, 0.3, and 0.45 cm, with each depth corresponding to defect features. The same simulations and analyses were done with a 160 kVp (79 keV avg) spectrum and a 480 kVp (218 keV avg) photon spectrum. FIG. 6 shows an image of the system with full collimation.

The fuel rod representation used was a natural enrichment UO2 rectangular parallelepiped (3×3.77×1.6 cm) with zirconium cladding (0.05 cm) on the +z parallelepiped surface. This was done with the knowledge that backscatter radiography would be difficult to accomplish throughout the width of the rod and that rastering by rotating an actual fuel rod about its length axis would in effect create a rectangular parallelepiped. In addition, two rectangular parallelepiped voids of thickness 0.05 cm and depth of 0.6 cm (grooves) transverse the width (y-axis) of the rod, with the z-max of the voids equaling the z-min of the zirconium cladding in order to represent the small amount of spacing between fuel pellets in a fuel rod. A spherical void defect (Void) (0.3 cm diameter) and palladium (Pd) rectangular parallelepiped defect (0.5× 0.3×0.15 cm) were both strategically placed in the fuel pellet so that the effects of each defect did not interfere with the effects of the other defect or with the grooves in the rod, both having z-max of 0.15 cm below the top surface of the zirconium cladding (referred to as deep). Palladium was chosen because it is a fission product of 235U and is generally considered a high-Z element. Additionally, the simulation was attempted for both X-ray source energies with the defects moved along the z-axis such that z-max would correspond to the bottom of the zirconium cladding, or 0.05 cm below the top surface (referred to as shallow).

Methods and Materials—Imaging and Image Processing

Raw data was created by using a rastering method of moving both the source and detector array in 1 mm increments over a fuel rod image that included both a portion of the fuel rod unaffected by grooves or defects, and a portion with grooves and defects. A total of $1 \times 10^7$ source particles were used for each position along the rastering path. Tallies were scored when one of the particles crossed the bottom surface of a detector. The same rastering method and the same tallies were used for both a base uncollimated case and a collimated test case. In the uncollimated case, each collimator length was selected such that the lower edge was coplanar with the bottom of the detector. In the collimated case, each collimator length was selected such that the critical depth corresponded to defect features in the "deep" case, specifically the top of both defects, bottom of the Pd defect, and bottom of the void defect. The collimator lengths that corresponded to the chosen critical depths were 4.52, 4.65, and 4.79 cm for the 0.15, 0.3, and 0.45 cm critical depths, respectively. One detector in all cases was left with a collimator length of 0 cm (uncollimated) in order to create a base case for depth analysis and to test the standard uncollimated backscatter imaging method.

To analyze the features of an image, specifically the presence and nature of a defect, the numeric results of each detector were normalized using Equation 1:

$$Xnorm = \frac{X - Xtrue}{\sqrt{Xtrue}}, \quad (1)$$

where Xnorm is the normalized count, X is the detected count, and Xtrue is the average of the count over the area of the fuel rod unaffected by the presence of any defects or grooves (Base). Xnorm can be interpreted as analogous to the idea of "signal versus background" commonly used. The base case is a selected area of the analyzed surface at each collimation length which is unaffected by defects or grooves for each detector. As a result, changes in the base case are solely a result of transmission through $UO_2$. The true X term can be interpreted as the standard deviation of the measurement due to expected Poisson statistics. The Poisson statistical nature of radiation measurement results in a general guideline that measurements must be at least 2σ different to be statistically relevant, so Eq. 1 was used to determine whether a numeric shift was the result of statistical variation or the presence of a defect. With this method, the results from detectors with different critical depths can be contrasted despite the decrease in absolute value of the detected signal as the critical depth increases throughout the rod, since the relative change from a portion of the rod unaffected by defects changes throughout the thickness of the rod due to defects.

Additionally, the relative contribution by a defect to a generated image can be determined in order to ascertain the nature of a defect from a single image. Specifically, a void defect differs from an absorption defect in that a void defect causes a bright "shadow" with proper collimation, in contrast to the dark "shadow" of an absorber or scattering material. Numerical results were analyzed graphically and compared using ImageJ, an open-source image-processing program. To partially isolate the contribution from a defect over the depth of the defect, we use $$RC = T - B, \quad (2)$$

where RC is the relative change in counts, T is the normalized count from a detector with critical depth at the top (−zmax) of the defect, and B is the normalized count from a detector with critical depth at the bottom (z-min) of the defect.

Preliminary Experimental Verification

Figure 7:
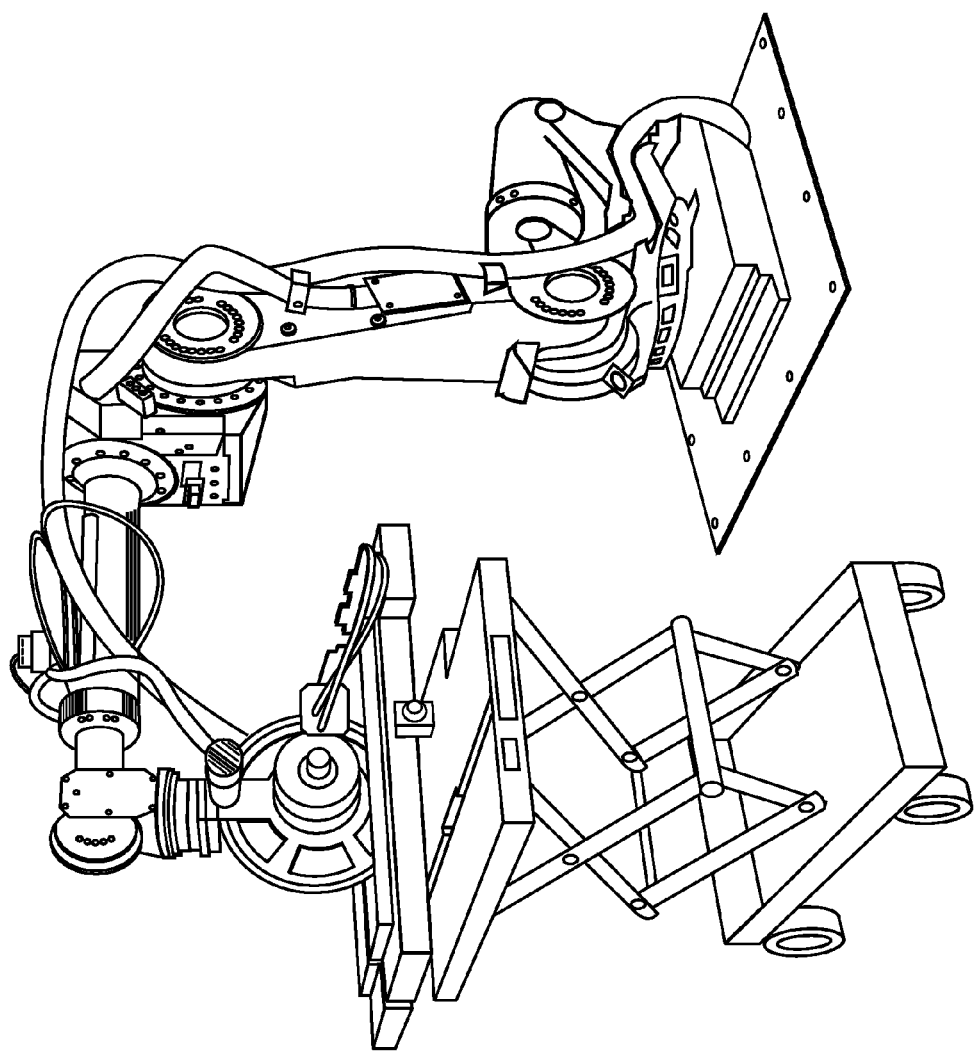
FIG. 7 is a picture of an imaging device used to visually inspect and verify mock-up fuel rods.
Figure 8:
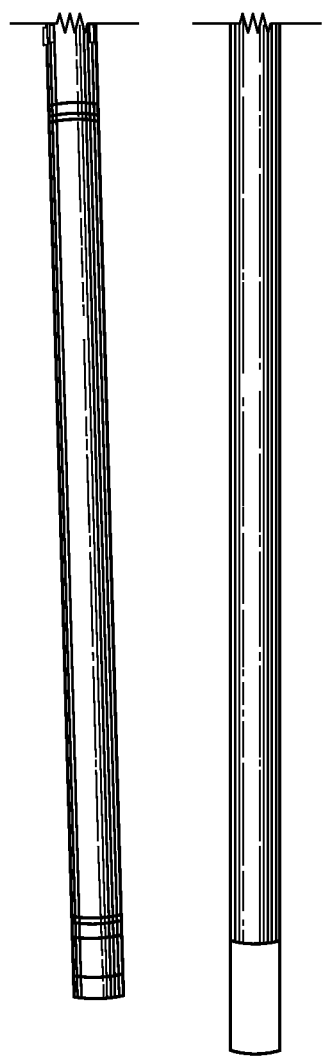
FIG. 8 is a picture of demonstration fuel rods imaged using imaging device.

In an attempt to experimentally verify the application of backscatter X-ray imaging to fuel rods, two mock fuel rods were imaged using the imaging device shown in FIG. 7. The mock fuel rods imaged are shown in FIG. 8.

The Scatter X-ray Imaging (SXI) device is owned and operated by Nucsafe, with all imaging done on their premises. The SXI system used four large surface area, plastic scintillator detectors and an X-ray tube with a maximum voltage of 160 kVp which was moved over the demonstration fuel rods. One mock fuel rod consisted of a short segment of $HfO_2$ pellets, bordered on both sides by a lower density material, encased in a Zircaloy-4 tube. The other mock fuel rod consisted of stainless steel pellets encased in a Zircaloy-4 clad pin (with a hold down spring) further encased in a stainless steel tube (a typical double encapsulated design for test reactor irradiation). Imaging was done with 0.1 mm pitch, and resultant images were analyzed using ImageJ.

Results for MCNP Simulation—160 kVp Spectrum

The number of photons that entered the detector for the case of a 160 kVp spectrum and defects with $Z_{max}$ being 0.15 cm below the top surface of the zirconium is shown in Table 1. Numbers are all averages for regions in which the source is directly over the specific area.

TABLE 1

Detector Counts for 160 kV spectrum

| | Critical Depth | | | |
|---|---|---|---|---|
| | 0 cm | 0.15 cm | 0.3 cm | 0.45 cm |
| | Detector Counts Per Critical Depth Deep Defects ($Z_{max}$ = 0.15 cm) | | | |
| Base | 29760 (172) | 1768 (42) | 1917 (43) | 2090 (45) |
| Void | 29761 (172) | 1768 (52) | 1916 (43) | 2090 (45) |
| Pd | 29752 (172) | 1768 (42) | 1915 (43) | 2088 (45) |
| | Shallow Defects ($Z_{max}$ = 0.05 cm) | | | |
| Base | 29760 (172) | 1768 (42) | 1917 (43) | 2089 (45) |
| Void | 26146 (161) | 1451 (38) | 1509 (38) | 1880 (43) |
| Pd | 19070 (138) | 528 (22) | 662 (25) | 684 (26) |

In the deep defect instance, there is no numerical distinction between the void, Pd defect, and the $UO_2$ itself. There is too much attenuation within the $UO_2$ for any relevant results in the case of deep defects. Relative changes in detector response due to defect presence are all insignificant compared to inherent statistical variation and thus were not calculated. In contrast, the z-max=0.05 cm case clearly demonstrates that there is a change in detector output due to defect presence. For example, the Pd defect changes detector response by amounts ranging from 28 standard deviations to 61 standard deviations, with similar results for the void defect (32-51). This change allows an image to be generated from the results, improving defect visualization, as shown in FIG. 9.

Figure 9:
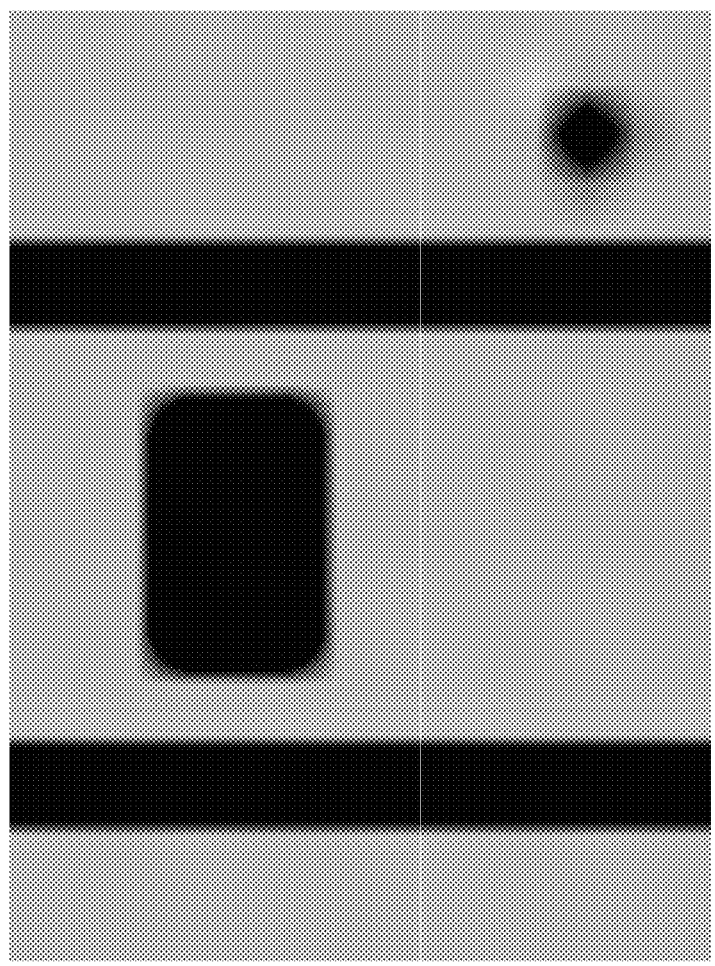
FIG. 9 is an image of defects from 0.3 cm critical depth at 160 kV of X-ray voltage.

FIG. 9 does not show any visible shadowing for the Pd defect, so it is not possible to characterize the Pd defect, though the Pd defect is clearly detected as a defect. The void defect is distinguishable as a void defect, though it is difficult; increased counts would be expected to improve the ability to characterize the void defect as well. However, the image does show the small spacing between fuel pellets and shows that both the void and Pd defects are detectable. The relative shift in detector output as a result of the void defect is smaller than that of the Pd defect, likely due to its smaller size and more spherical shape than the rectangular parallelepiped shape of the Pd defect. It is clear that the 160 kVp source simulation is capable of detecting the presence of surface defects of the defect sizes used.

Results for MCNP Simulation—480 kVp Spectrum

The rastering process used for the 160 kVp spectrum was also used for the 480 kVp spectrum. Table 2 gives the number of counts recorded using a 480 kVp spectrum and provides similar information to that found in Table 1 for the 160 kVp spectrum.

TABLE 2

Detector counts for the 480 kVp spectrum: Numerical values are actual tally values, multiplied by source particles ($1 \times 10^7$).

| | Critical Depth | | | |
|---|---|---|---|---|
| | 0 cm | 0.15 cm | 0.3 cm | 0.45 cm |
| Base | 38791 (196) | 6223 (78) | 6365 (79) | 6585 (81) |
| Void | 38421 (196) | 6156 (78) | 6297 (79) | 6492 (80) |
| Pd | 38323 (196) | 6237 (78) | 6251 (79) | 6532 (80) |
| Shallow Defects ($Z_{max}$ = 0.05 cm) | | | | |
| Base | 38791 (196) | 6223 (78) | 6365 (79) | 6586 (81) |
| Void | 32169 (179) | 5358 (73) | 5412 (73) | 5708 (75) |
| Pd | 24662 (157) | 6608 (84) | 6434 (80) | 6752 (82) |

In the deep defect case, the void defect systematically decreases the detector response but only by statistically insignificant changes (0.8-1.8 standard deviations). This is similar to its behavior for the Pd defect (0.1-2.3 standard deviations), which is statistically relevant only for the uncollimated case. It is suspected that the low relative change in detector response for the deep defect scenario is only a result of the small counts, so the same analysis was performed using $6 \times 10^7$ initial particles in comparison to the $1 \times 10^7$ originally used; the results are shown in Table 3.

TABLE 3

Detector counts for the 480 kVp spectrum, $6 \times 10^7$ particles

| | Critical Depth | | | |
|---|---|---|---|---|
| | 0 cm | 0.15 cm | 0.3 cm | 0.45 cm |
| Base | 232231 (481) | 37573 (193) | 38671 (196) | 40093 (200) |
| Void | 228703 (478) | 37650 (194) | 38548 (196) | 39611 (199) |
| Pd | 229898 (479) | 37216 (192) | 38226 (195) | 40033 (200) |

The shallow defect portion of Table 2 provides some interesting information. The uncollimated, simple backscatter method shows very large relative changes due to both defects. The Pd defect in all collimation lengths for the shallow case is easily detected, but the void defect varies in its ability to be detected, notably having only a 0.9 standard deviation shift for the 0.3 cm critical depth case. This implies that the RSD method is inefficient for the shallow defect case, but the uncollimated backscatter method is sufficient to detect the presence of a defect.

Table 3 shows similar behavior to Table 2, with the only major difference being the numerical increase in counts. The uncollimated detector is capable of detecting both the Pd and the void defect, while the collimated detectors are much less efficient in detection, particularly for the Pd defect, and do not provide statistically significant results. It appears that the change in photon attenuation as a result of the Pd defect is too small at high energies for efficient detection and analysis using the RSD method. This is not to say that the RSD method fails, and indeed the statistics did improve as one would expect, but the relative change in detector response is very small. Therefore, it is reasonable to conclude that the RSD method does work for imaging fuel inside the fuel rod, but it is highly inefficient. As expected, however, the uncollimated detector provides statistically significant results, implying that backscatter imaging without application of the RSD method is capable of detecting defect presence.

Figure 10:
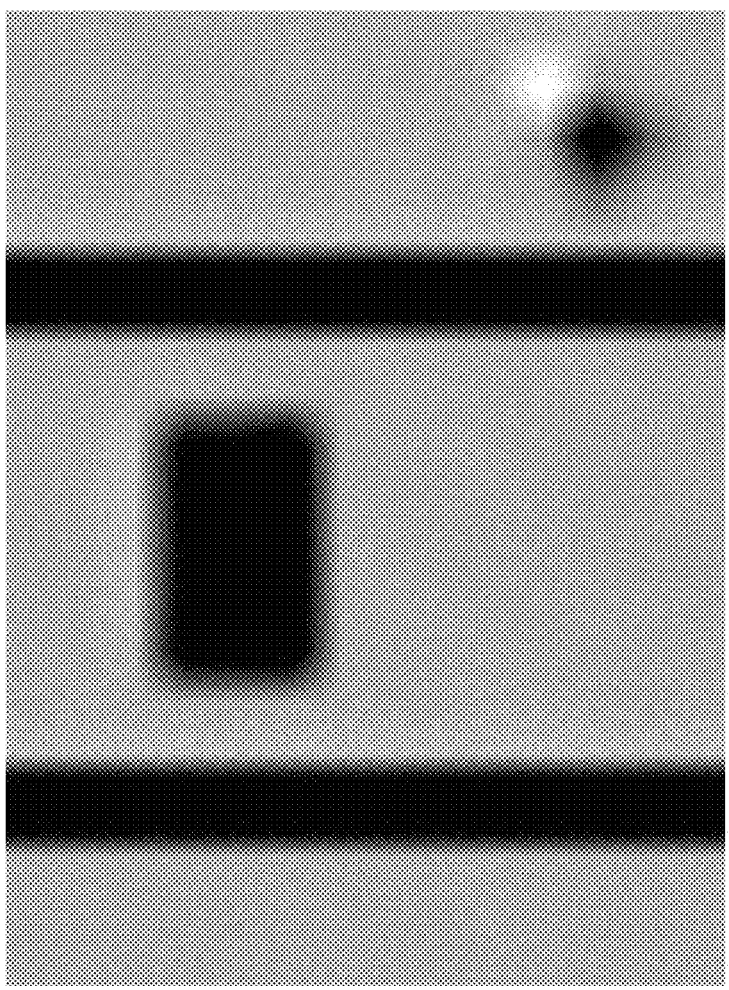
FIG. 10 is a 480 kV fuel rod image from an uncollimated detector at $1.0 \times 10^7$ particles.
Figure 11:
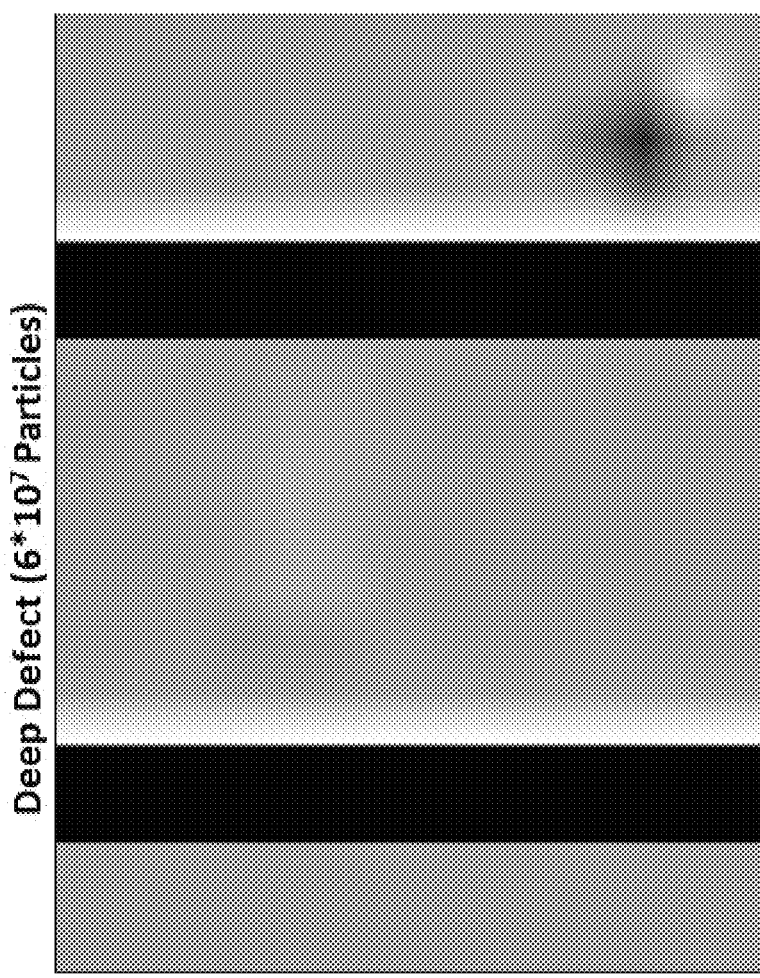
FIG. 11 is a 480 kV fuel rod image from an uncollimated detector at $6.0 \times 10^7$ particles.

FIGS. 10 and 11 show the images generated from both the shallow defect and the deep defect cases for high-energy photons, respectively. In contrast to FIG. 9, FIGS. 10 and 11 show superior results, which demonstrate the superior ability of the 480 kVp spectrum not only to detect defects but to characterize them. The deep defect case clearly shows the presence of the void defect in the bottom right, as expected. Furthermore, the void defect and the grooves within the rod demonstrate bright "shadows," indicating their nature as voids. Similar behavior is seen for the shallow defect case, though the magnitude and range over which the effect is observed is not as great. Interestingly, the bright "shadow" is also seen for the Pd defect, suggesting that it, in comparison to $UO_2$, is a mild void defect. If the Pd defect were an absorbing material, a dark shadow would be expected.

Results: Comparison Between Spectra

Figure 12:
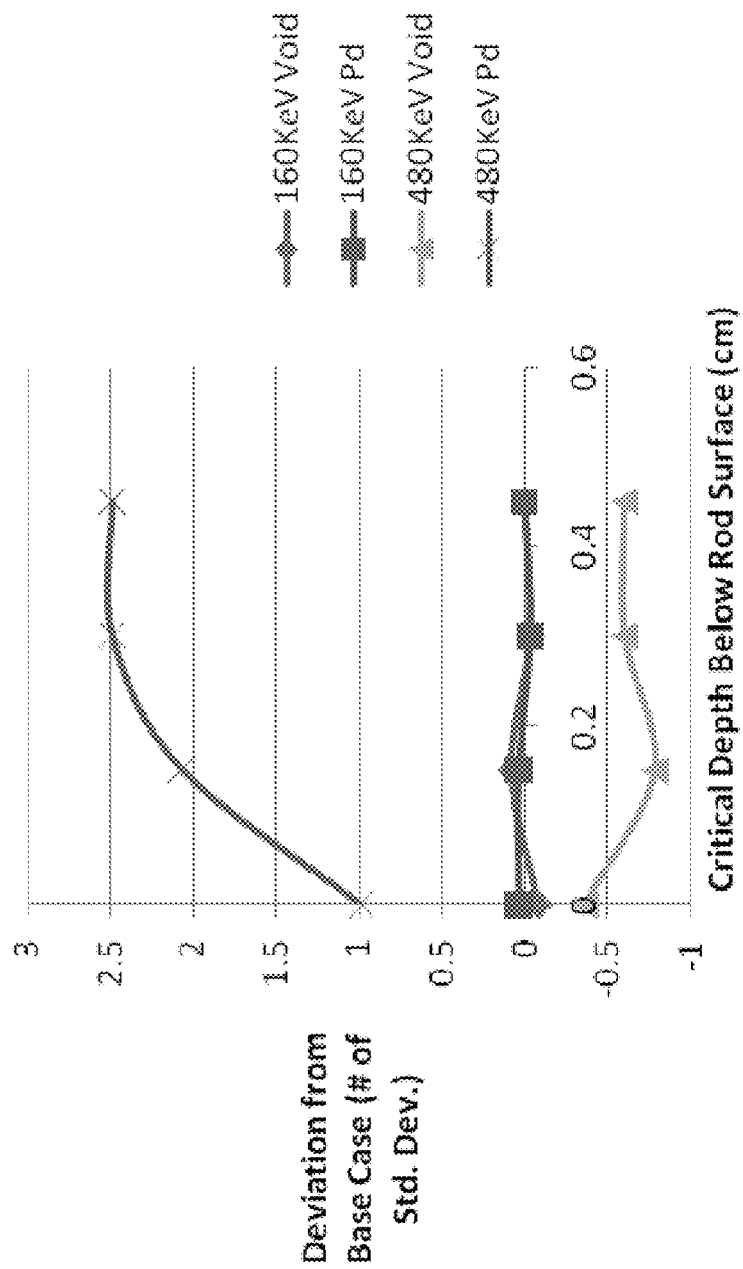
FIG. 12 is a graph of deep defect comparison of spectra.

An important question for system optimization is the energy optimization for either shallow or deep defect responses. The comparison between the 160 kVp spectrum and the 480 kVp spectrum for the deep defect case is shown in FIG. 12.

Figure 13:
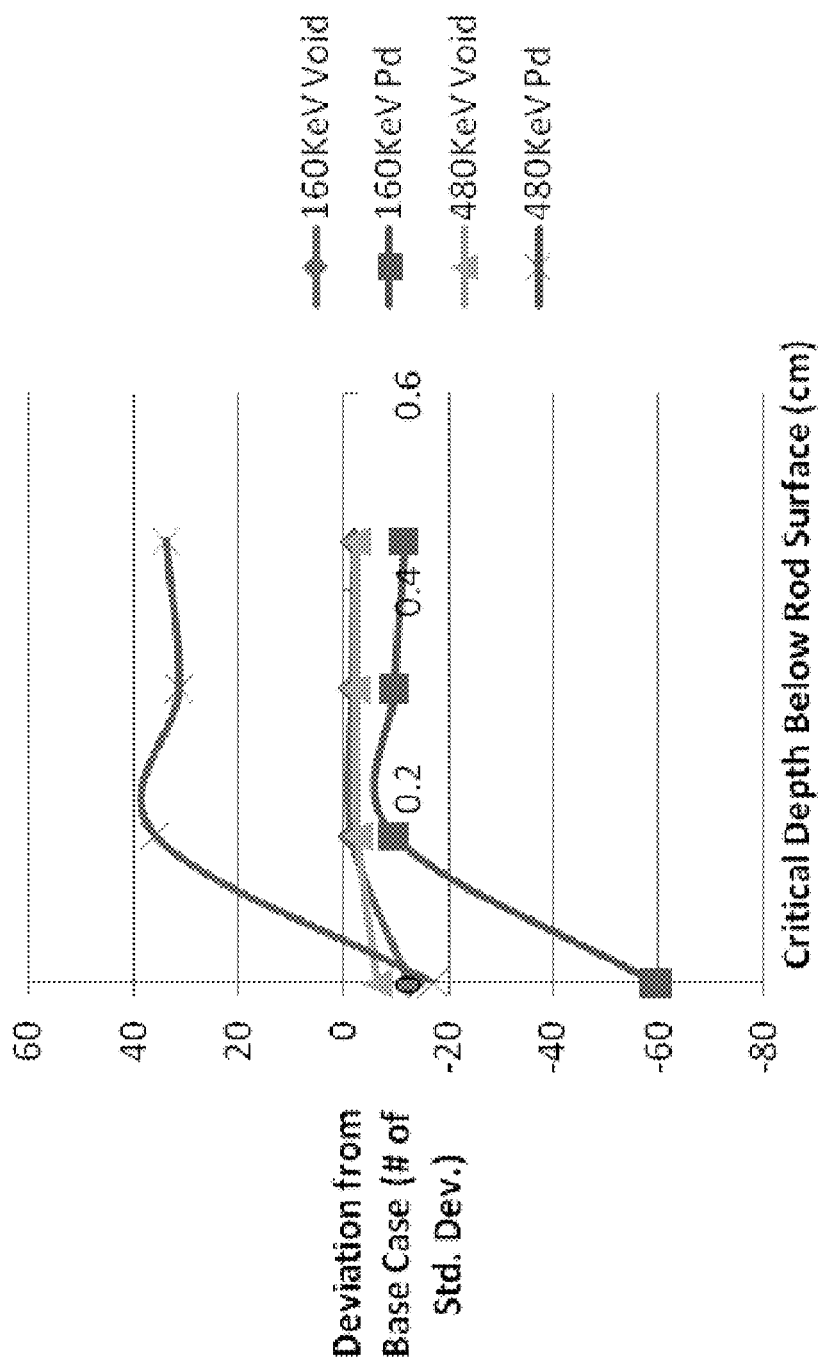
FIG. 13 is a graph of shallow defect comparison of spectra.

It appears from a quick glance that the 480 kVp spectrum is superior to the 160 kVp spectrum at detecting the presence of defects that are relatively deep within the fuel pellet. This is not surprising due to the increased range of the photons, and it would be expected that the same procedure at even deeper critical depths would provide better analysis of defect depth. Even with the 480 kVp spectrum, however, it is still impossible to distinguish the presence of a defect while maintaining statistical validity using a relatively small number of source particles, although it is possible using a very large number of source particles. As a result it is reasonable to assume that while the 480 kVp spectrum is capable of detecting a defect that is relatively deep within a fuel rod, it is inefficient. The same process to compare the qualities of both systems in analyzing the "deep" case was used to compare both systems with regard to the "shallow" case, as shown in FIG. 13.

Similarly to the deep defect situation, it appears that the 480 kVp spectrum is superior to the 160 kVp spectrum at detecting a defect. However, some behaviors were unexpected: neither energy spectrum appears particularly useful for detecting the void defect, and the 160 kVp and 480 kVp spectra do not exhibit the same behavior with regard to the Pd defect. It appears that at lower energies, such as those seen in the 160 kVp spectrum, the Pd defect behaves very much like an absorber, thus decreasing the counts, while at high energies the Pd defect is thin enough and with low enough attenuation coefficient to be treated as a void. An absorber would be expected to have a negative deviation throughout, as seen in the 160 kVp results, while a void would be expected to start with a negative deviation due to additional exit attenuation, but increase to a positive deviation throughout the defect thickness, as seen in the 480 kVp results. It is clear then that Pd is not a true absorber defect or scatter defect in relation to $UO_2$. In practical scenarios, to at least some extent many materials would be considered a void in comparison to $UO_2$ due to the relative density and attenuation inherent in $UO_2$. $UO_2$ not only is very dense, but its $Z_{eff}$ (effective atomic number) is also very high in comparison to most commonly used materials, which explains the high attenuation of photons in $UO_2$.

It is notable that the numeric values of the deviation (−12.4 for the 160 kVp spectrum and −6.6 for the 480 kVp) signify that the system is capable of detecting the void defect, but probably because of the size difference, the system is superior in detecting the relatively large Pd defect. A larger void defect of the same geometry as the Pd defect would be expected to provide equally significant results.

Throughout each simulation, counts generally increased with increasing critical depth from 0.15 to 0.45 cm. While the increase in counts ranged from negligible to over 20%, much of the increase could be attributed to defect presence impacting the results in various ways (Pd acting as a void, etc.), so an increase within areas unaffected by defect presence is significantly more interesting, particularly since a decrease in counts is expected. The reasonable explanation is that the specific location of each detector created preferential scattering towards locations that then scattered in the direction of the detector. The simulation process was not repeated with each detector having its critical depth changed, but if there were a significant change in counts, then the assumption would be verified that the locations of each detector resulted in the systematic increase in counts. Although not performed, changing which detectors correspond to which critical depth would verify the preferential scattering.

Results from SXI Imaging

Figure 14:
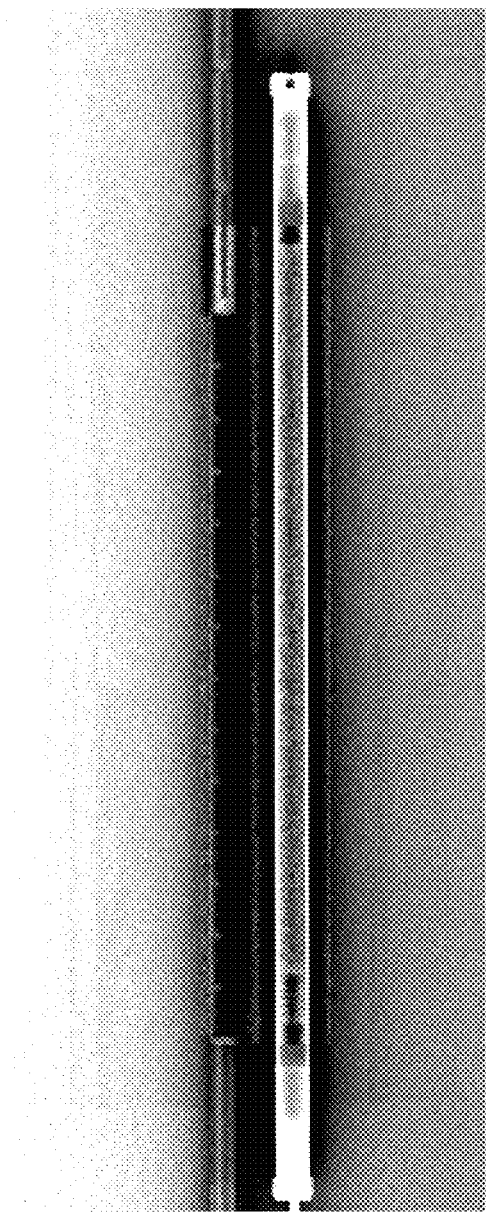
FIG. 14 is an image of fuel rods scanned with an SXI instrument.

The numeric results from the SXI imaging process were converted into an image using ImageJ, which is shown in FIG. 14. The upper fuel rod is composed of steel pellets inside a Zircaloy-4 clad encased in a steel rod, and the bottom fuel rod is composed of $HfO_2$ pellets inside a Zircaloy-4 rod. A number of distinguishing characteristics of both rods are readily apparent from the image. It is easy to differentiate between pellets in the $HfO_2$ rod and difficult to differentiate between pellets in the steel rod. One of the reasons for this is the chamfered ends of the $HfO_2$ pellets vs. the flat ends of the steel pellets. The lower density pellets bordering the $HfO_2$ pellets are readily visible, and it is possible to detect the spring and Zircaloy-4 pins and caps within the outer stainless steel cladding. However, there is a distinct difference in the relative ability of the system to distinguish the steel pellets from the steel cladding and the individual $HfO_2$ pellets from the Zircaloy cladding. The system creates a clear visual distinction between hafnium and Zircaloy, two materials of significantly different Z (and therefore electron density), and even is capable of distinguishing individual pellets. This is due to the chamfered ends of the $HfO_2$ pellets, which produce the equivalent of large void defects between pellets, as shown in FIG. 14. This shows that significant void defects are easily identified using X-ray backscatter imaging. The same ease of distinction is not possible in the steel pellet and steel cladding case, however. It is possible, though not easy, to distinguish the pellets from the cladding, but the flat edges of the pellets render it impossible to discern between individual pellets with the resolution used in scanning. Decreasing the pixel size used in the scanning process would be expected to improve the image resolution and possibly allow for individual pellet differentiation in the steel rod. If the pellets were replaced with $UO_2$, as in an actual fuel rod, the ability of the system to detect individual pellets would be expected to have a similarly pronounced effect due to the similar difference in photon attenuation between Zircaloy and $UO_2$ and Zircaloy and $HfO_2$. While no experimental investigation was done on the system's ability to perform defect or depth analysis, it is capable of distinguishing a high-Z material from a low-Z and is capable of detecting individual pellets.

CONCLUSION

Compared with traditional methods of fuel rod imaging, backscatter X-ray imaging provides not only surface data about fuel pellets contained within zirconium cladding but also some degree of depth analysis. A 160 kVp X-ray source was used to test the abilities of the radiography by selective detection (RSD) method for both deep defects and shallow defects, and the results were compared with those of a 480 kVp X-ray source by using Monte Carlo simulations. It was found that the deep defects (z-max=0.15 cm below rod surface) were detectable only by the 480 kVp spectrum, though it was very inefficient in doing so when Radiography by Selective Detection (RSD) was used. The 160 kVp spectrum was capable of detecting both a Pd defect and a void defect in the shallow case (z-max=0.05 cm below rod surface), but it exhibited some behavior inconsistent with the 480 kVp spectrum. Furthermore, all detectable defects were detected by the uncollimated detector, signifying that simple backscatter X-ray imaging does suffice for detection, though depth characterization requires the RSD method. More research is needed into energy optimization versus defect depth. A tradeoff exists between increased photon penetration depth and efficiency loss due to increased forward scattering for higher-energy photon energy interactions.

While the disclosure has been described in terms of specific embodiments, it is evident in view of the foregoing description that numerous alternatives, modifications and variations will be apparent to those skilled in the art. The various embodiments of the present disclosure can be implemented solely, or in combination with any other embodiments described herein unless incompatibility among various embodiments are expressly stated or otherwise clear to one of ordinary skill in the art. Accordingly, the disclosure is intended to encompass all such alternatives, modifications and variations which fall within the scope and spirit of the disclosure and the following claims.

What is claimed is:

1. A method of imaging a high-Z material-including structure by X-ray backscatter imaging, said method comprising:
    irradiating a target including a high-Z material-including structure with an incident X-ray radiation from an X-ray source, said high-Z material-including structure including at least one element having an atomic number of at least 57;
    detecting a backscattered X-ray radiation from said target with at least one detector-collimator assembly positioned to block a fraction of said backscattered X-ray radiation originating at depths less than a critical depth from a top surface of said target; and
    constructing an image of said target employing at least data collected at said at least one detector-collimator assembly, said image including information on structural discontinuity of said high-Z material-including structure.

2. The method of claim 1, wherein said at least one element is selected from Lanthanides and Actinides.

3. The method of claim 1, wherein said at least one element is a fissile material.

4. The method of claim 1, wherein said high-Z material-including structure includes an oxide, a nitride, a carbide, a fluoride, or a boride of said at least one element.

5. The method of claim 1, wherein said high-Z material-including structure includes a nuclear fuel material that is encased in a cladding.

6. The method of claim 5, wherein said high-Z material-including structure includes $UO_2$.

7. The method of claim 5, wherein said high-Z material-including structure includes a manufactured nuclear fuel rod in which atomic ratio of fissile atoms to fission products is greater than 5:1.

8. The method of claim 5, wherein said high-Z material-including structure includes a spent nuclear fuel rod that has been removed from a nuclear reactor.

9. The method of claim 1, wherein said target includes a stack of said high-Z material-including structure and a cladding that encloses said high-Z material-including structure, and wherein said critical depth is within said high-Z material-including structure during said irradiating and said detecting.

10. The method of claim 1, further comprising scanning different areas of said target with said incident X-ray radiation by providing a relative movement between said target and said X-ray source.

11. The method of claim 10, wherein a distance between said target and said at least one detector-collimator assembly is maintained at a constant value during said scanning.

12. The method of claim 10, wherein said relative movement is provided continuously while said target is continuously irradiated with said incident X-ray radiation.

13. The method of claim 10, wherein said relative movement is provided between each sequential irradiation of different areas of said target with said incident X-ray radiation.

14. The method of claim 10, wherein said relative movement is provided by maintaining said target stationary and moving said X-ray source and said at least one detector-collimator assembly.

15. The method of claim 10, wherein said X-ray source and said at least one detector-collimator assembly moves at the same rate of movement in a same direction throughout said relative movement.

16. The method of claim 15, wherein said target is a nuclear fuel rod, and said relative movement is provided by moving said X-ray source and said at least one detector-collimator along a lengthwise direction of said nuclear fuel rod.

17. The method of claim 10, wherein said relative movement is provided by maintaining said X-ray source and said at least one detector-collimator assembly stationary while moving said target.

18. The method of claim 1, wherein said incident X-ray radiation includes photons having energy in a range from 150 keV to 800 keV.

19. The method of claim 1, wherein said at least one element having an atomic number of at least 57 is an Actinide, and said incident X-ray radiation includes photons having energy in a range from 500 keV to 700 keV.

20. The method of claim 19, wherein said Actinide is uranium, and said high-Z material-including structure includes $UO_2$.

21. The method of claim 1, wherein said image of said target is constructed by processing said data collected at said at least one detector-collimator assembly with a computing device.

22. The method of claim 1, further comprising
changing a distance between said at least one detector-collimator assembly and said target, wherein said at least one detector-collimator assembly becomes positioned to block of another fraction of said backscattered X-ray radiation originating at depths less than a second critical depth from said top surface of said target, wherein said second critical depth is different from said critical depth; and
irradiating said target with said incident X-ray radiation from said X-ray source while said changed distance is maintained.

23. The method of claim 22, further comprising constructing a second image of said target from additional data collected at said at least one detector-collimator assembly while said changed distance is maintained, said second image including additional information on structural discontinuity of said high-Z material-including structure.

24. The method of claim 23, wherein said image and said second image are 2-dimensional images, and said method further comprises constructing a 3-dimensional image of said target from a set of images including at least said image and said second image.

25. The method of claim 22, wherein said image is a 3-dimensional image that is constructed from said data and additional data collected at said at least one detector-collimator assembly while said changed distance is maintained.

* * * * *